(12) United States Patent
Siegel et al.

(10) Patent No.: US 12,313,798 B2
(45) Date of Patent: *May 27, 2025

(54) HELICALLY-ARRANGED POSITRON EMISSION TOMOGRAPHY DETECTOR UNITS

(71) Applicant: Siemens Medical Solutions USA, Inc., Malvern, PA (US)

(72) Inventors: Stefan B. Siegel, Knoxville, TN (US); Ziad Burbar, Knoxville, TN (US); Inki Hong, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/632,604

(22) Filed: Apr. 11, 2024

(65) Prior Publication Data

US 2024/0302550 A1 Sep. 12, 2024

Related U.S. Application Data

(63) Continuation of application No. 17/632,405, filed as application No. PCT/US2020/018240 on Feb. 14, 2020, now Pat. No. 11,982,780.

(51) Int. Cl.
| | |
|---|---|
| *G01T 1/29* | (2006.01) |
| *A61B 6/00* | (2024.01) |
| *A61B 6/03* | (2006.01) |
| *A61B 6/42* | (2024.01) |
| *G01T 1/20* | (2006.01) |

(52) U.S. Cl.
CPC ............ *G01T 1/2985* (2013.01); *A61B 6/037* (2013.01); *A61B 6/4266* (2013.01); *A61B 6/4275* (2013.01); *A61B 6/4435* (2013.01); *G01T 1/20181* (2020.05); *G01T 1/20182* (2020.05)

(58) Field of Classification Search
CPC .............. G01T 1/2985; G01T 1/20181; G01T 1/20182; A61B 6/037; A61B 6/4266; A61B 6/4275; A61B 6/4435
See application file for complete search history.

(56) References Cited

U.S. PATENT DOCUMENTS

| | | | |
|---|---|---|---|
| 4,669,103 A * | 5/1987 | Barnea | A61B 6/032 378/10 |
| 9,599,731 B2 | 3/2017 | Schulz et al. | |
| 2005/0109943 A1 | 5/2005 | Vaquero et al. | |
| 2005/0111610 A1 * | 5/2005 | De Man | G01N 23/046 378/10 |

(Continued)

FOREIGN PATENT DOCUMENTS

| | | | |
|---|---|---|---|
| DE | 19905975 | 9/2000 | |
| WO | 9901736 | 1/1999 | |
| WO | WO-2022090257 A1 * | 5/2022 | ............. A61B 6/027 |

OTHER PUBLICATIONS

International Search Report for Corresponding PCT Application No. PCT/US2020/018240, dated Oct. 20, 2020.

*Primary Examiner* — David P Porta
*Assistant Examiner* — Casey Bryant

(57) ABSTRACT

A detector unit for a PET imaging system is disclosed that includes a gantry having a patient-receiving tunnel, where the detector unit includes a plurality of detector elements in a helical arrangement around an axial axis of the PET imaging system.

18 Claims, 5 Drawing Sheets

(56) References Cited

U.S. PATENT DOCUMENTS

| | | |
|---|---|---|
| 2010/0128956 A1 | 5/2010 | Yamaya et al. |
| 2016/0157791 A1 | 6/2016 | Shizukuishi |
| 2016/0183893 A1* | 6/2016 | Zhang .................. A61B 6/0407 250/363.05 |
| 2022/0291402 A1* | 9/2022 | Siegel .................... A61B 6/037 |

* cited by examiner

HELICALLY-ARRANGED POSITRON EMISSION TOMOGRAPHY DETECTOR UNITS

CROSS REFERENCE TO RELATED APPLICATIONS

This application is a continuation of U.S. patent application Ser. No. 17/632,405, filed Feb. 2, 2022, which is a 371 of PCT Patent Application No. PCT/US2020/018240, filed Feb. 14, 2020, which is hereby incorporated by reference in its entirety and relied upon

BACKGROUND

Positron emission tomography (PET) is widely used in medical diagnostics. PET allows in vivo visualization and quantification of metabolic activities. PET uses the special properties of positron emitters and positron annihilation in order to quantitatively determine the function of organs or cell regions. With this technique, appropriate radiopharmaceuticals marked with radionuclides are administered to the patient prior to the examination. As they decay, the radionuclides emit positrons that after a short distance interact with an electron, causing what is termed annihilation to occur. This results in two gamma quanta that fly apart in opposite directions (offset by 180°). The gamma quanta are detected by two opposing PET detector elements within a specific time window (coincidence measurement), as a result of which the annihilation site is localized to a position on the line connecting the two detector modules.

Upon detecting a gamma quantum, each detector element generates an event record that specifies the time and the detection location, i.e., the corresponding detector element. This information is passed to a fast logic unit and compared. If two events coincide within a maximum time interval, it is assumed that a gamma decay process is taking place on the connecting line between the two associated detector elements. The PET image is reconstructed using a tomography algorithm, i.e., so-called back-projection.

The detector elements are typically arranged in the form of partial or full rings that are configured to be arranged around an axial axis of the PET system. Due to mechanical constraints, a gap is typically present between adjacent rings of detectors. These gaps can impact the spatial resolution of the system and sensitivity for reconstructed image planes that straddle these gaps.

U.S. Pat. No. 9,599,731, titled Positron Emission Tomography and/or Single Photon Emission Tomography Detector, discloses an imaging system that includes a magnetic resonance portion and a PET portion. The PET portion includes a two dimensional array of detector tiles. Adjacent tiles along each column are spaced apart by a gap and neighboring tiles along each row about each other and are offset from each other by a non-zero distance that is less than a length of a tile.

SUMMARY

In one aspect, a positron emission tomography imaging system includes a gantry having a patient-receiving tunnel and a first detector unit and a second detector unit housed inside the gantry. The first detector unit includes a plurality of detector elements arranged in a helical arrangement around an axial axis of the PET imaging system. The second detector unit includes a plurality of detector elements arranged in a helical arrangement around the axial axis. Each of the detector elements in the second detector unit is spaced apart from a corresponding detector element in the first detector unit along a direction parallel to the axial axis of the PET imaging system by an axial gap. Each detector element in the first and second detector units has an axial position measured parallel to the axial axis from an entrance of the patient-receiving tunnel to a geometric center of the detector element. The first and second detector units each have its plurality of detector elements arranged so that a set of the plurality of detector elements is positioned such that each detector element in the set is offset from an adjacent detector element in the detector unit in a direction parallel to the axial axis of the PET imaging system such that a maximum difference between axial positions of detector elements in the detector unit is less than or equal to the axial gap.

In another aspect, a detector unit for a positron emission tomography imaging system that has a gantry having a patient-receiving tunnel includes a plurality of detector elements arranged in a helical arrangement configured to be disposed around an axial axis of the PET imaging system. When the detector unit is installed in the PET imaging system, each detector element has an axial position measured parallel to the axial axis of the PET imaging system from an entrance of the patient-receiving tunnel to a geometric center of the detector element. The plurality of detector elements are arranged so that a set of the plurality of detector elements is positioned such that each detector element in the set is offset from an adjacent detector element in a direction parallel to the axial axis of the PET imaging system such that a maximum difference between axial positions of detector elements in the detector unit is less than or equal to an axial gap between each of the plurality of detector elements and a corresponding detector element in a second detector unit when the detector unit and the second detector unit are installed in the PET imaging system.

BRIEF DESCRIPTION OF THE DRAWINGS

The features of the embodiments described herein will be more fully disclosed in the following detailed description, which is to be considered together with the accompanying drawings wherein like numbers refer to like parts.

DETAILED DESCRIPTION

Figure 1:
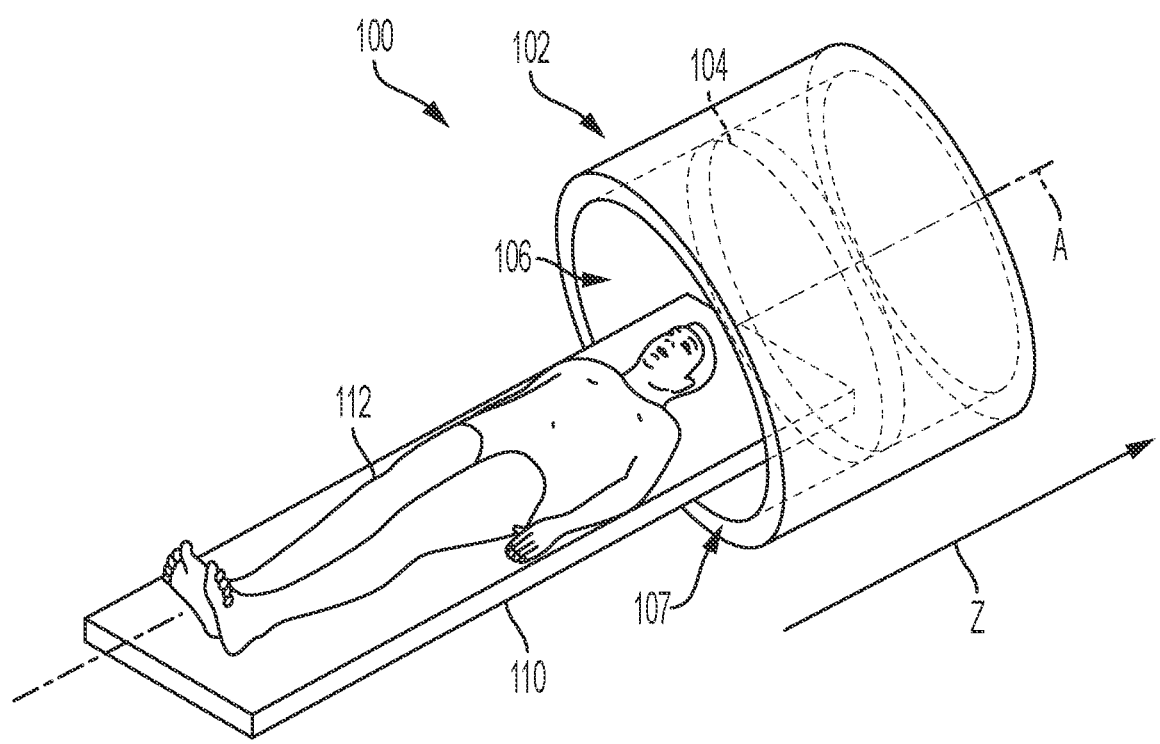
FIG. 1 shows a schematic illustration of a PET imaging system.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

The imaging systems described herein include detector elements that are arranged in a helical pattern. The helical arrangement of the detector elements provides a configuration in which the axial gaps between axially aligned detector elements are circumferentially offset. As a result, artifacts and discontinuities in images produced using the imaging systems are reduced.

FIG. 1 shows an imaging system 100 such as a PET imaging system, including a PET scanner gantry 102. In some embodiments, the imaging system 100 further includes other imaging modalities, such as, for example, a CT scanner or an MRI scanner. In accordance with one embodiment described herein, the PET scanner gantry 102 houses a plurality of detector units 104, each arranged in a helical arrangement in the circumferential direction (i.e., transaxial direction) surrounding a patient-receiving tunnel 106. Each of the detector units 104 can be supported by the gantry 102. The patient-receiving tunnel 106 defines an axial axis A, which is oriented substantially parallel to a spatial direction Z. The tunnel 106 has an entrance 107 from which a patient 112 can be introduced to the tunnel 106.

Figure 2:
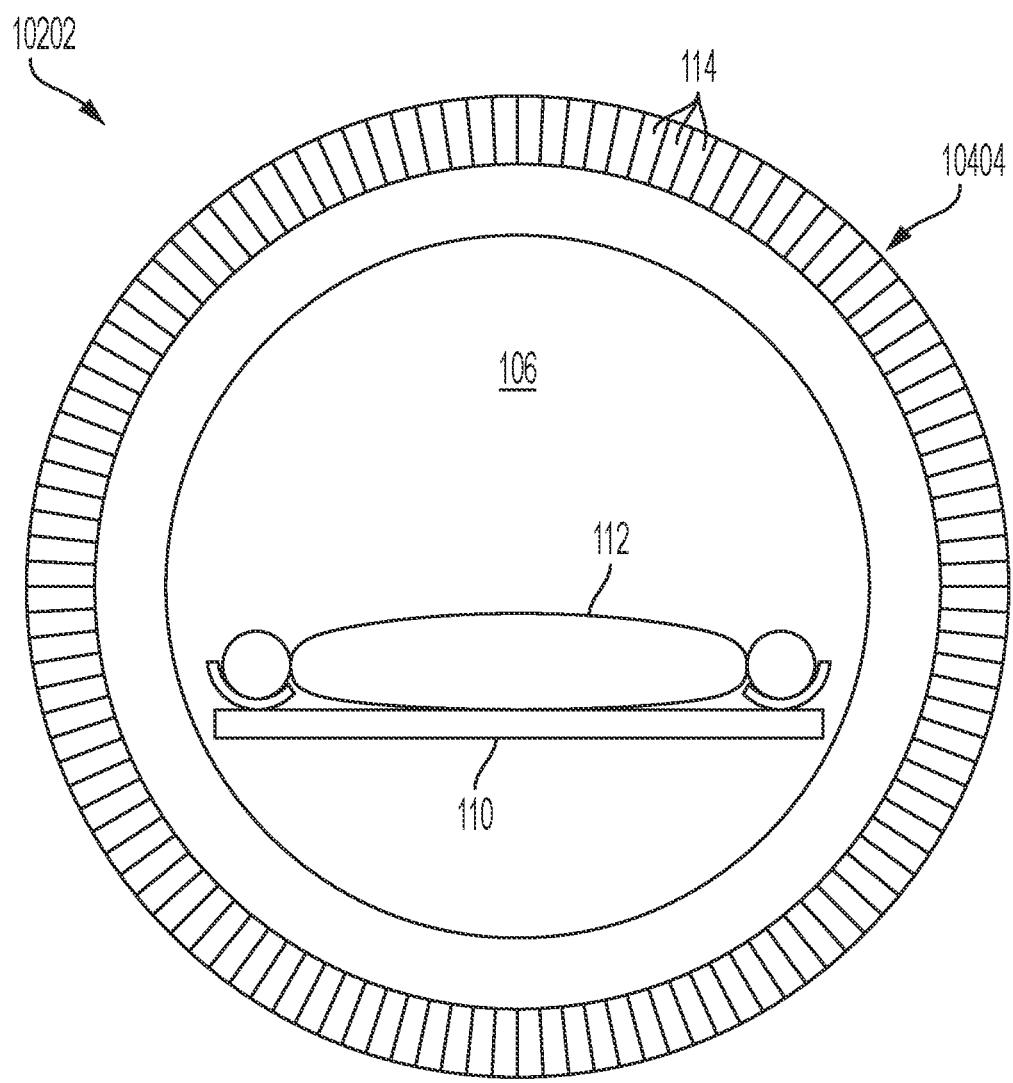
FIG. 2 shows a schematic cross-sectional view of the PET imaging system of FIG. 1, wherein the section is taken through one of the detector units with a patient positioned within the detector tunnel.

FIG. 2 shows the PET scanner gantry 102 portion of the imaging system 100 in a sectional view. The cross-section is taken through one of the detector units 104 housed in the gantry 102. Arranged inside the patient-receiving tunnel 106 is a patient bed 110 upon which the patient 112 can be positioned. The patient's torso and arms are shown in cross-section in FIG. 2.

As shown in FIG. 2, each detector unit 104 includes a plurality of detector elements 114 (e.g., scintillation detectors) arranged outside the patient-receiving tunnel 106. Each detector unit 104 can further include an avalanche photodiode array (APD) preceded by an array of lutetium oxyorthosilicate (LSO) crystals and an electrical amplifier circuit (AMP). However, the imaging systems 100 described herein are not limited to detector units 104 having the APD photodiode array preceded by an array of LSO crystals, and other kinds of photodiodes, crystals and devices can equally be used for detection purposes. In addition, the detector units 104 can include detector electronics, including an electrical amplifier circuit and further electronic components, not shown.

Figure 3:
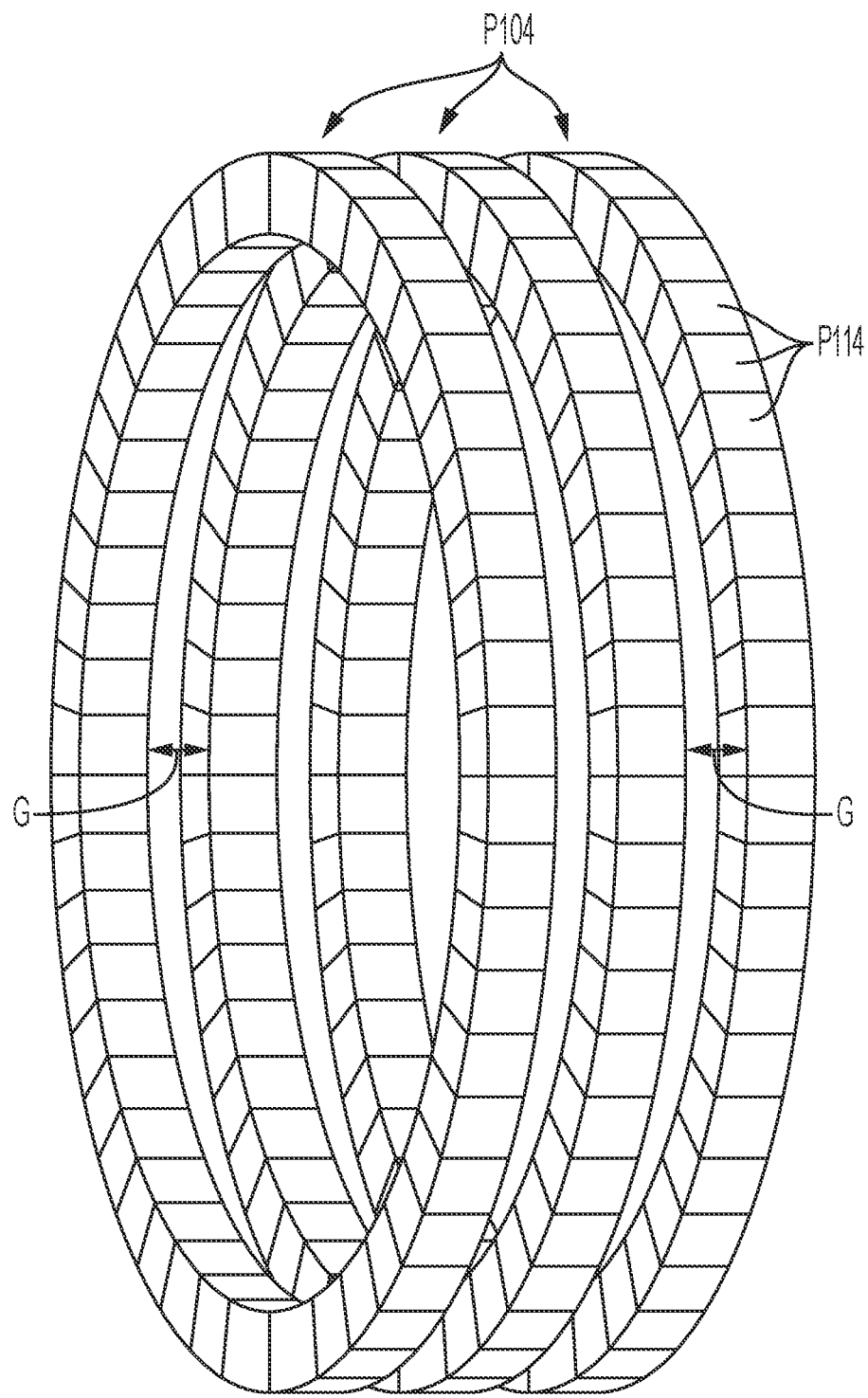
FIG. 3 shows a schematic illustration of a subset of detector units of a prior art PET imaging system, according to one embodiment described herein.

FIG. 3 shows a schematic perspective view of a subset of detector units P104 in typical prior art imaging systems. In the prior art systems, the detector elements P114 in a given detector unit P104 are arranged in a ring. In the ring configuration, each detector element P114 in a given detector unit P104 is aligned with the other detector elements P114 in that detector unit P104 in the transaxial (i.e., circumferential) direction. In other words, each of the detector elements P114 in the detector unit P104 have the same axial position-measured from the entrance 107 of the tunnel 106, for example.

Additionally, an axial gap G is present between each detector unit P104 in a direction parallel to the axial axis A of the imaging system 100. Thus, the gap G is present between each detector element P114 in a detector unit P104 and an adjacent detector element P114 in an adjacent detector unit P104. The gap G exists because of mechanical constraints that prevent the detector units P104 from directly abutting against one another. As shown in FIG. 3, the gaps between adjacent detector elements P114 create a continuous gap around the circumference of the patient receiving tunnel P106. These continuous gaps can create discontinuities in images produced using such prior art systems, particularly for image planes that straddle these gaps.

Figure 4:
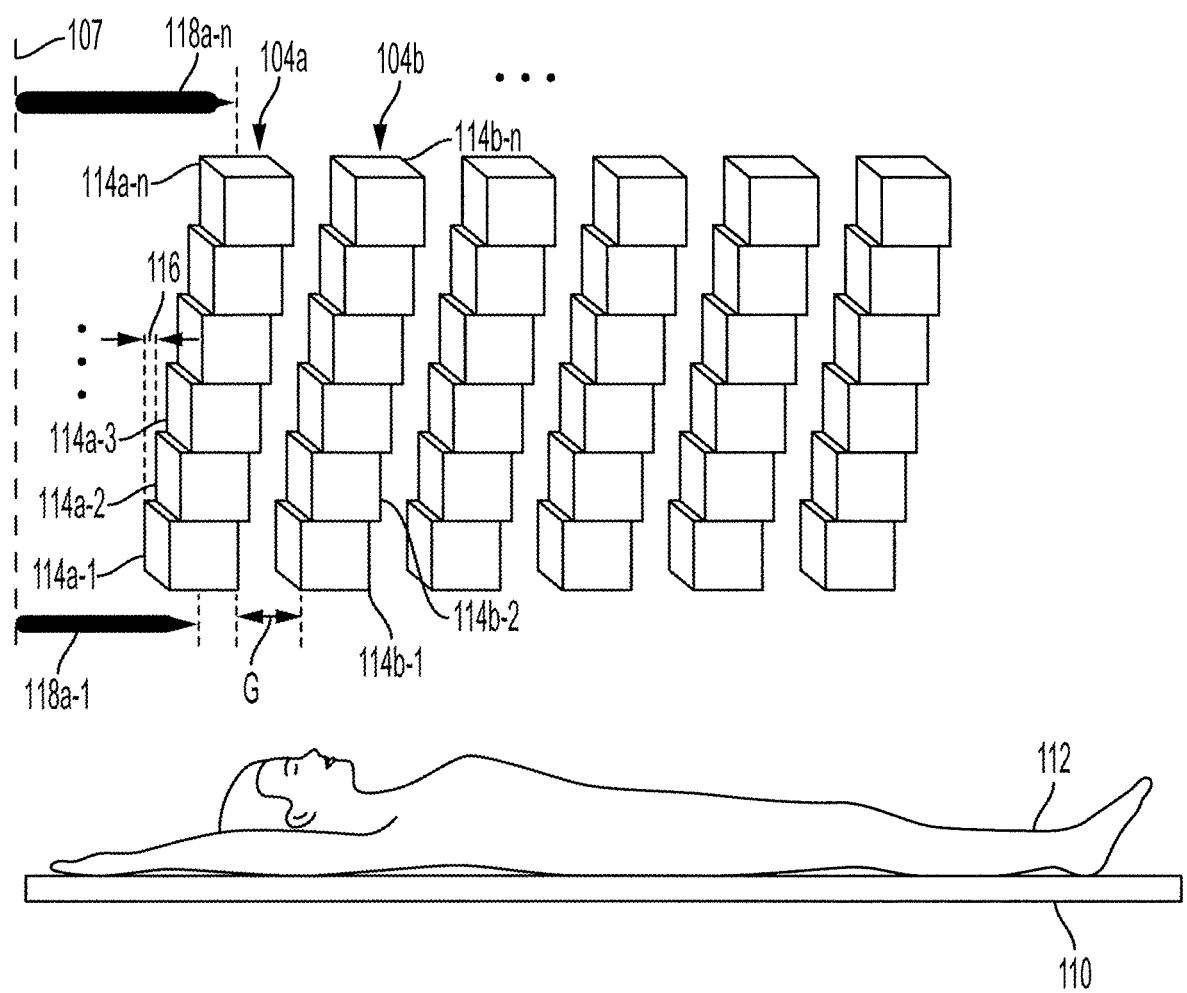
FIG. 4 shows a schematic illustration of detector units of a PET imaging system in relation to a patient in the patient tunnel, according to one embodiment described herein, where the detector units are shown in a planar illustration for ease of visualization.

An example of the novel configuration for detector elements 114 in detector units 104 according to the present disclosure is illustrated in FIG. 4. FIG. 4 shows a schematic illustration of a flattened detailed view of adjacent sections of the detector units 104 of the imaging systems 100 described herein. FIG. 4 shows the detector units 104 as if one were looking at the detector units 104 from within the patient tunnel 106 and illustrates the detector units 104a, 104b, . . . and a patient 112 who is in the patient tunnel. It should be understood that the detector units 104 shown in FIG. 4 are schematic and shown in enlarged view for illustration purposes. Thus, their sizes are not to scale with the patient 112 shown in the figure. It should also be noted that only a subset of the detector elements 114 are shown. As shown, in some embodiments of the detector unit 104 of the present disclosure, a set of the PET detector elements 114 in a given detector unit 104 (i.e., one or more detector elements 114) are sequentially shifted in the axial direction with respect to other PET detector elements 114 in the same detector unit 104. The shifting of the detector elements 114 creates a helical arrangement of the detector elements 114.

The spatial relationship of two detector units 104 are described in more detail below. It should be understood that the described spatial relationship can apply to all of the detector units 104 in the PET scanner gantry 102. The imaging system 100 can include a first detector unit 104a including a first set of detector elements 114a and a second detector unit 104b including a second set of detector elements 114b. For illustration purposes, the detector elements 114 in each detector unit 104 are referred to as 114x-1 to 114x-n, where x indicates the detector unit of which the detector element is a part and n is the total number of detector elements in each of the detector units 104. Thus, for example, the detector elements in the second detector unit 104b will be referred to as 114b-1 to 114b-n.

An axial gap G is present between each detector element 114a of the first detector unit 104a and the corresponding detector elements 114b of the second detector unit 104b, with the corresponding detector element 114b being the detector element 114b that is adjacent to the detector element 114a in the first detector unit 104a. In other words, the corresponding detector element 114b is linearly aligned with the relevant detector element 114a parallel to the axial axis A of the imaging system 100. For example, an axial gap G is present between the first detector element 114a-1 and the second detector element 114*b*-1. The axial gap G may be due to mechanical or other constraints that prevent the detector elements 114 from directly contacting. In some embodiments, the axial gap G is approximately equal to the crystal pitch of the detector elements 114. In some embodiments, the axial gap G between each of the detector elements 114*a* in the first detector unit 104*a* and the corresponding detector element 114*b* in the second detector unit 104*b* is equal (or uniform) for each of the detector elements; however, this is not required and the axial gap G can vary. As described above, in prior art PET scanners, these axial gaps can cause issues with the spatial resolution of the scanner and can lead to image artifacts and discontinuities. This is particularly the case in systems in which the axial pitch of the detector crystals in the detector elements 114 has been reduced such that the axial gap G is approximately the same as the axial pitch of the detector crystals in the detector elements 114.

As shown in FIG. 4, in embodiments of the PET scanner 102 described herein, in each of the detector units 104, the detector elements 114 are shifted axially such that the axial gap G between the detector elements 114*a*-1 . . . 114*a*-*n* of the first detector unit 104*a* and the detector elements 114*b*-1 . . . 114*b*-*n* of the second detector unit 104*b* are not circumferentially (or transaxially) aligned. For example, the axial gap G between detector element 114*a*-1 and detector element 114*b*-1 is not aligned with the axial gap G between detector element 114*a*-2 and detector element 114*b*-2. By arranging the detector elements 114 in each detector unit 104 in this manner, the spatial resolution and image artifact issues described above with respect to prior art systems can be reduced or eliminated.

The arrangement of the detector elements 114 will be described using the first detector unit 104*a* as an example. As shown in FIG. 4, a set of the detector elements 114 of the first detector unit 104*a* are positioned such that each detector element 114*a* in the set is offset from an adjacent detector element 114*a* in the detector unit 104*a* in a direction parallel to the axial axis A of the imaging system 100. While FIG. 4 shows an embodiment in which each detector element 114*a* is in the set of detector elements that is shifted relative to the adjacent detector elements, it should be understood that this is not required. For example, in other embodiments, every third detector element 114*a* is shifted relative to its adjacent detector elements. Alternatively, the set of shifted detector elements can include every fourth detector element, every fifth detector element, etc. As shown in FIG. 4, each detector element in the set of offset detector elements is shifted by an offset distance 116 from an adjacent detector element in the first detector unit 104*a* along a direction parallel to the axial axis A of the PET scanner 102 by an offset distance 116 (e.g., detector element 114*a*-2 is shifted relative to detector element 114*a*-1). Preferably, each of the detector elements 114*a* in the set of offset detector elements is shifted in the same axial direction (i.e., the detector elements 114*a* do not alternate back and forth). As shown in FIG. 4, each of the second detector elements 114*a* can be offset from an adjacent second detector element 114*a* by the same offset distance 116 (i.e., the offset distances 116 are uniform). In other embodiments, the offset distance 116 varies (e.g., the offset distance 116 between detector element 114*a*-1 and detector element 114*a*-2 is different than the offset distance 116 between detector element 114*a*-2 and detector element 114*a*-3). Because of the shift of the detector elements 114*a*, the detector elements 114*a* of the first detector unit 104*a* have different axial positions 118 (e.g., as measured from the entrance 107 of the tunnel 106 to the geometric center of the detector unit 114*a*). For example, the axial position 118*a*-*n* of the detector element 114*a*-*n* is different than the axial position 118*a*-1 of the detector element 114*a*-1. It should be understood that, although described with reference to a single detector unit 104*a* for illustration purposes, one or more of the detector units 104 of the PET scanner 102 can have the shifted arrangement of detector elements 114 described herein. In one preferred embodiment, all of the detector units 104 of the PET scanner 102 have the shifted arrangement of the detector elements 114 described herein.

Figure 5:
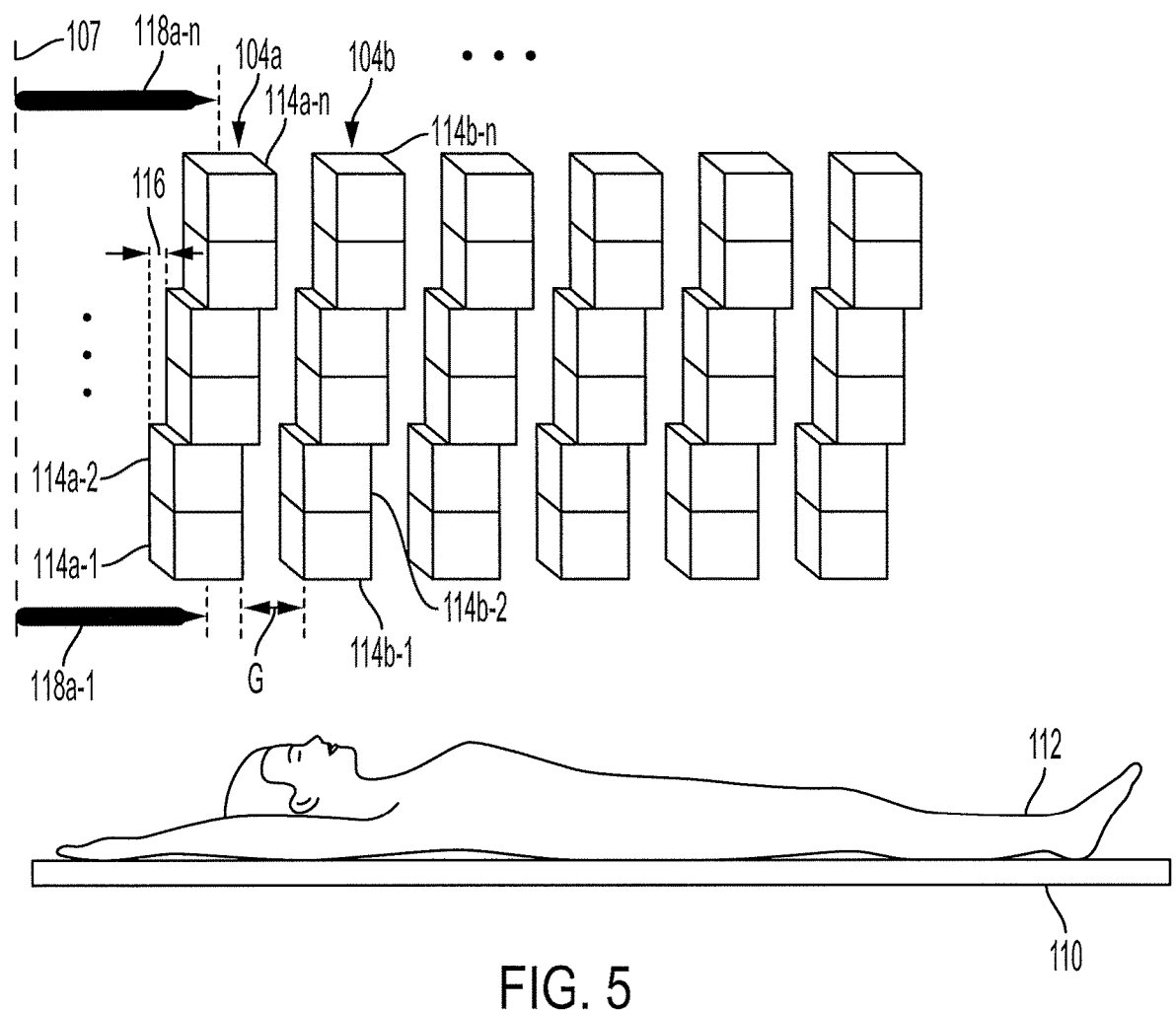
FIG. 5 shows a schematic illustration of detector units of a PET imaging system in relation to a patient in the patient tunnel, according to another embodiment described herein, where the detector units are shown in a planar illustration for ease of visualization.

Another embodiment will now be described with reference to FIG. 5 which shows the detector units 104 as if one were looking at the detector units 104 from within the patient tunnel 106 and illustrates the detector units 104*a*, 104*b*, . . . and a patient 112 who is in the patient tunnel. It is not required that every one of the detector elements 114 in a detector unit 104 be shifted axially and other configurations can be used. In one embodiment, shown in FIG. 5, each of the detector elements 114 in the set of offset detector elements is a member of a group of n consecutive detector elements 114, with each of the n consecutive detector elements in the respective group having a same axial position (e.g., detector elements 114*a*-1 and 114*a*-2 have the same axial position 118*a*-1). Each group of n consecutive detector elements 114 in the detector unit 104 is offset from detector elements 114 adjacent to the group in the respective detector unit 104 by an offset distance (e.g., offset distance 116 shown in FIG. 5). It should be understood that each member of the set of offset detector elements can be a member of a different group of n consecutive detector elements. For example, in the embodiment shown in FIG. 5, the first detector unit 104*a* can be arranged in groups of two detector elements 114*a*, with each group of two detector elements 114*a* offset from the adjacent groups of two detector elements 114*a*. Although FIG. 5 illustrates two detector elements 114*a* in each group of consecutive detector elements, it should be understood that other number of detector elements 114*a* can be included in each group (e.g., three detector elements, four detector elements, etc.). Further, the offset distances 116 between detector elements 114*b* need not be uniform. For example, in some embodiments, the offset distances 116 between different detector elements 114*a* can be different at different transaxial positions. Again, it should be understood that, although described with reference to a single detector unit 104*a* for illustration purposes, one or more of the detector units 104 of the PET scanner 102 can have the shifted arrangement of detector elements 114 described herein and illustrated in FIG. 5. In one preferred embodiment, all of the detector units 104 of the PET scanner 102 have the shifted arrangement of the detector elements 114 described herein and shown in FIG. 5.

In some embodiments, the sum of the offset distances 116 of the detector elements 114 in a detector unit 104 (e.g., the sum of the offset distances 116 between each detector element 114*a* and the adjacent detector element 114*a*) is less than or equal to the axial gap G between the detector elements 114 (e.g., between detector element 114*a*-1 and detector element 114*b*-1). In other words, the maximum difference between axial positions (e.g., as measured from the entrance 107 of the tunnel 106 of the PET scanner 102 to the geometric center of the detector element 114) of the detector elements 114 in a detector unit 104 is less than or equal to or no more than the gap G. For example, the difference between axial position 118*a*-*n* of detector element 114*a*-*n* and the axial position 118*a*-1 of detector element 114*a*-1 is less than or equal to the gap G. Hence, the gap G between any second detector element 114*b* and a corresponding one of the first detector elements 114*a* is "filled"

by one or more detector elements 114a in the first detector unit 104a. In other words, the gap G between each pair of the first 114a and second 114b detector elements are staggered or offset in a direction parallel to the axial axis A such that the PET scanner 102 does not have a continuous gap extending in the transaxial direction that can cause artifacts and other problems with spatial resolution. In addition, the arrangement of the detector elements 114 disclosed herein can be used to improve the axial sampling of the imaging system 100 due to the detector elements 114 being positioned at different axial positions within the gantry 102.

For example, in embodiments in which each of the detector elements (e.g., detector element 114a-2) is offset from an adjacent detector element (e.g., detector element 114a-1) by a uniform or equal offset distance 116, the uniform offset distance 116 (i.e., the offset distance between a detector element and its adjacent detector element) can be less than or equal to:

$$\text{Uniform Offset Distance} \leq G/N$$

where N is the number of detector elements 114 in a detector unit 104 and G is the axial gap between a detector element 114 in the detector unit 104 and a corresponding detector element 114b in an adjacent detector unit 104 (e.g., between detector element 114a-1 and detector element 114b-1).

In one embodiment, each detector unit 104 includes 40 detector elements 114 and the axial gap G is equal to 4 mm. For such an embodiment, the axial offset distance 116 is equal to 0.1 mm.

In addition to eliminating or reducing artifacts and discontinuities in images, the helical detector units 104 described herein can also be used for long axial field of view systems with minimal image quality degradation. The helical arrangement of the detector units 104 can also reduce the number of detector elements 114 required for a given axial field of view.

It will be understood that the foregoing description is of exemplary embodiments of this invention, and that the invention is not limited to the specific forms shown. Modifications may be made in the design and arrangement of the elements without departing from the scope of the invention.

What is claimed is:

1. A detector unit for a positron emission tomography (PET) imaging system that includes a gantry having a patient-receiving tunnel, wherein the detector unit comprising:
   a plurality of detector elements in a helical arrangement around an axial axis of the PET imaging system;
   each detector element is offset from an adjacent detector element along a direction parallel to the axial axis of the PET imaging system by an axial gap such that a maximum difference between axial positions of detector elements in the detector unit is less than or equal to the axial gap.

2. The detector unit of claim 1, wherein each detector element has an axial position measured parallel to the axial axis from an entrance of the patient-receiving tunnel to a geometric center of the detector element,
   wherein the plurality of detector elements are arranged so that a set of the plurality of detector elements is positioned such that each detector element in the set is offset from an adjacent detector element in the detector unit in a direction parallel to the axial axis.

3. The detector unit of claim 2, wherein each detector element is offset from that detector element's adjacent detector elements in a direction parallel to the axial axis.

4. The detector unit of claim 3, wherein each detector element is offset from that detector element's adjacent detector elements in the detector unit by a uniform offset distance.

5. The detector unit of claim 2, wherein the detector unit consists of 40 detector elements.

6. The detector unit of claim 1, wherein each detector element is offset from that detector element's adjacent detector elements in a direction parallel to the axial axis.

7. The detector unit of claim 6, wherein each detector element is offset from that detector element's adjacent detector elements in the detector unit by a uniform offset distance.

8. The detector unit of claim 1, wherein the detector unit consists of 40 detector elements.

9. A positron emission tomography (PET) imaging system, comprising:
   a gantry having a patient-receiving tunnel;
   a detector unit housed inside the gantry, wherein the detector unit comprises a plurality of detector elements in a helical arrangement around an axial axis of the PET imaging system;
     wherein each detector element is offset from an adjacent detector element along a direction parallel to the axial axis of the PET imaging system by an axial gap such that a maximum difference between axial positions of detector elements in the detector unit is less than or equal to the axial gap.

10. The PET system of claim 9, wherein each detector element has an axial position measured parallel to the axial axis from an entrance of the patient-receiving tunnel to a geometric center of the detector element, and
   wherein the detector elements are arranged so that a set of the plurality of detector elements is positioned such that each detector element in the set is offset from an adjacent detector element in the detector unit in a direction parallel to the axial axis of the PET imaging system.

11. The PET system of claim 10, wherein each detector element is offset from that detector element's adjacent detector elements in a direction parallel to the axial axis.

12. The PET system of claim 11, wherein each detector element is offset from that detector element's adjacent detector elements in the detector unit by a uniform offset distance.

13. The PET system of claim 10, wherein each detector element in the set of detector elements is a member of a respective group of n consecutive detector elements, with each of the n consecutive detector elements in the respective group having a same axial position, and wherein each group is offset from detector elements adjacent to the group by an offset distance.

14. The PET system of claim 13, wherein each group of n consecutive detector elements is offset from the detector elements adjacent to the group by a uniform offset distance.

15. The PET system of claim 10, wherein the detector unis consists of 40 detector elements.

16. The PET system of claim 9, wherein each detector element is offset from that detector element's adjacent detector elements in a direction parallel to the axial axis.

17. The PET system of claim 16, wherein each detector element is offset from that detector element's adjacent detector elements in the detector unit by a uniform offset distance.

18. The PET system of claim 9, wherein the detector unit consists of 40 detector elements.

\* \* \* \* \*